US00PP08917P

United States Patent [19]

Drewlow

[11] Patent Number: Plant 8,917

[45] Date of Patent: Sep. 27, 1994

[54] IMPATIENS PLANT NAMED ALLEGRO

[75] Inventor: Lyndon W. Drewlow, Ashtabula, Ohio

[73] Assignee: Mikkelsens, Inc., Ashtabula, Ohio

[21] Appl. No.: 163,769

[22] Filed: Dec. 9, 1993

[51] Int. Cl.[5] ..... A01H 5/00

[52] U.S. Cl. ..... Plt./87.6

[58] Field of Search ..... Plt. 87.6

[56] References Cited

U.S. PATENT DOCUMENTS

PP 77892 2/1992 Drewlow ..... Plt./87.6

*Primary Examiner*—James R. Feyrer

*Attorney, Agent, or Firm*—Foley & Lardner

[57] ABSTRACT

A new and distinct cultivar of Impatiens plant named Allegro, characterized by its double-flower form having ten petals, white flower color, flower diameter of 5.5 to 6.0 cm, yellow-green pedicels, five leaves in a whorl, relatively short dark green leaves with cream variegation around the midrib, continuously flowering, highly self-branching and floriferous habit, ability to tolerate both high and low temperatures, and its adaptability to production in 10 cm up to 154–25 cm pots.

2 Drawing Sheets

The present invention relates to a new and distinctive cultivar of Impatiens plant, botanically known as Impatiens, commercially known as New Guinea Impatiens, and known by the cultivar name Allegro.

The new culture was developed in a controlled breeding program conducted by the inventor Lyndon W. Drewlow in Ashtabula, Ohio. Allegro was created by crossing Mikkelsen Seedling No. 90-118-2 (seed parent) with Mikkelsen Seedling No. 90-106-5 (pollen parent). Both parents are proprietary cultivars used in the breeding program.

Asexual reproduction by terminal or stem cuttings, carried out by or under the supervision of the inventor at Ashtabula, Ohio, has shown that the unique features of this new impatiens are stabilized and are reproduced true to type in successive propagations.

The following combination of characteristics distinguish the new impatiens from both its parent varieties and other cultivated impatiens of this type known and used in the floriculture industry. The description includes reference to comparison cultivars Innocence, disclosed in U.S. Plant Pat. No. 7,789 and Minuet, disclosed in a pending application of the inventor.

1. Allegro is a representative of an entirely new class of New Guinea impatiens that have ten flower petals, double the number of petals of the five petal single-flower types such as Innocence. Minuet is another cultivar in the double-flowered group.

2. Allegro has a white flower with a slight cream cast while Innocence has an entirely white flower.

3. Allegro has a flower diameter of 5.5 to 6.0 cm, similar to Minuet but larger than the 5.0 to 5.5 cm flower diameter of Innocence.

4. Both Allegro and Innocence have dark green leaves with cream variegation around the midrib of leaves, with the basal end of leaf being the most variegated. Minuet has a solid green leaf.

5. The upper leaf surface of Allegro is moderately hirsute while both Minuet and Innocence have a glabrous upper leaf surface.

6. Allegro has a leaf length of 7.0 to 8.0 cm, much shorter than the leaf lengthss of Innocence (11.0 to 12.0 cm) and Minuet (10.0 to 11.0 cm). All three are similar in width at 3.0 to 3.5 cm.

7. Allegro is 5 to 7 days later to bloom than Innocence as it takes the double flower with ten petals longer to develop and open than the five petals of the single-flowered Innocence. Allegro is similar in bloom date to Minuet.

8. The standard petal of the lower whorl and the standard-like petal of the upper whorl of petals overlap with the wing petals in the flowers of Minuet and Allegro to form a round flower, whereas in Innocence there is a gap between the standard petal and the wing petals which results in a long narrow flower.

9. Allegro has yellow-green flower pedicels, while Innocence has a light pinkish cast to the pedicels and Minuet has green flower pedicels.

10. Allegro has the shortest ciliate on leaf margins, with Innocence having the longest and Minuet intermediate.

In the photographic drawings, the color photo at the top illustrates in perspective view the overall appearance of Allegro, with the colors being as true as it is reasonably possible to obtain in a color reproduction of this type. The color photo was taken on Sep. 24, 1993 under natural light under 40% saran in a shaded glass greenhouse in Ashtabula, Ohio on a sunny day. The black and white photo on the bottom shows three (3) views of a typical flower of the new cultivar.

The following is a detailed description of my new cultivar, based on plants produced in greenhouses in Ashtabula, Ohio during the summer season of the year. Plants were grown in 15 cm pots and measurements were taken 18 weeks after rooted cuttings were planted. Height measurements were taken from the soil line of the container. The plants were grown at 65°–68° F. night temperatures under 3000–4000 foot candles of light, and with 250 ppm nitrogen, 75 ppm potassium, and 250 ppm phosphorous nutritional levels, with trace elements added. Habit of growth, foliage coloration, leaf variegation, size of leaves and flower size will be influenced by nutritional and environmental conditions, without, however, any variance in the genotype.

Color references are made to The Royal Horticultural Society Colour Chart except where general terms of ordinary dictionary significance are used.

Parentage: A controlled cross between female parent Mikkelsen Seedling No. 90-118-2 and male parent Mikkelsen Seedling 90-106-5.

Propagation:

(A) *Type cutting.*—Stem tip is 15 mm long and will develop 4 to 5 cm long in 18 to 21 days.

(B) *Time to root.*—8–10 days at 23° C. summer; 10–12 days at 20° C. winter.

(C) *Rooting habit.*—Heavy, fibrous.

Plant description:

(A) *Form and habit of growth.*—Mounded, dense, hightly self-branched; intermediate in height; flowering over the leaf canopy; continuous flowering, vigorous growing herb.

(B) *Foliage description.*—Deep green with yellow-green midrib and cream-colored variegation around midrib, approximately two-thirds the way up the leaf; variegation is greater with higher light levels. (1) Size: 7 to 8 cm long and 3.0 to 3.5 cm wide for average mature leaf. (2) Shape: Lanceolate to oval with acuminate apex and acute base. (3) Texture: Upper surface moderately hirsute and lower surface is glabrous. (4) Margin: Finely serrated with fine ciliate. (5) Color: Young foliage, top side is 146A variegated with 151A, under side is 146B; Mature foliage, top side is 147A variegated with 160B, under side is between 147B and 147C. (6) Veination: Pinnate, green in color.

Flowering description:

(A) *Flowering habits.*—Flowers continuously from leaf whorl in a progrssively orderly manner with one flower per leaf axil. When the last flower in a leaf whorl opens the first flowers in the leaf whorl above starts to open. It takes 5 to 7 days for a mature bud to fully open and the flower may last two weeks or longer depending on environment.

(B) *Natural flowering season.*—Indeterminant and continuous; quantity of flowering increases with increasing levels of light.

(C) *Flower buds.*—Ellipsoidal, flowers perfect; greenish-yellow in color; 4.5 cm long spur with green tip on mature bud with throat behind the ovary and originating from the major sepal.

(D) *Flowers borne.*—On individual yellow-green pedicels 3.5 cm long from a whorl of usually five leaves. Flowering is progresive around the whorl as buds and leaves develop with one flower per leaf axil being normal.

(E) *Quantity of flowers.*—Highly floriferous because of self-branching nature of plant, long-lasting flowers, and full appearance of double flowers.

(F) *Diameter of flower.*—5.5 to 6.0 cm.

(G) *Petals.*—(1) Shape: Heart, keel of bottom whorl of petals is largest. (2) Color: Top side in summer when opening is 155D, under side is 155D except area of 144D around midrib of standard petal. (3) Number of petals: Ten. (4) Size of petals: Standard: Only one true standard in lower whorl; corresponding petal in upper whorl has both standard and keel characteristics. Wings: Two sets of wing petals, with one petal smaller than other in each set. Keel: Two sets of keel petals, with each petal in a set being of equal size.

(H) *Reproductive organs.*—(1) Stamens: Five (5) in number. (a) Anther: Hooded shape; color is white. (b) Pollen color: White. (2) Pistils: (a) Stigma shape: Five (5), segmented column; color is whitish green. (b) Style color: Whitish green. (c) Ovaries: Five (5) in number; size is 6 mm when mature; color is green.

Disease resistance: No significant insect or disease problems noted to date.

OTHER IMPORTANT CHARACTERISTICS

1. Self-branching characteristic, mounded habit, and intermediate height make Allegro suitable for 10 cm pot production, but cultivar is vigorous enough for 15 and 25 cm pot production as well.

2. allegro can withstand both high temperatures and sunlight as well as low temperatures (40° to 50° F.), thus, extending the outside growing season and locating the cultivar can be planted.

3. The ten flower petals result in a much fuller looking flower as compared to the normal five petals. Thus, a double-flowered plant having the same number of flowers as a single-flowered plant will be substantially more colorful.

I claim:

1. A new and distinct cultivar of Impatiens plant named Allegro, as illustrated and described.

* * * * *

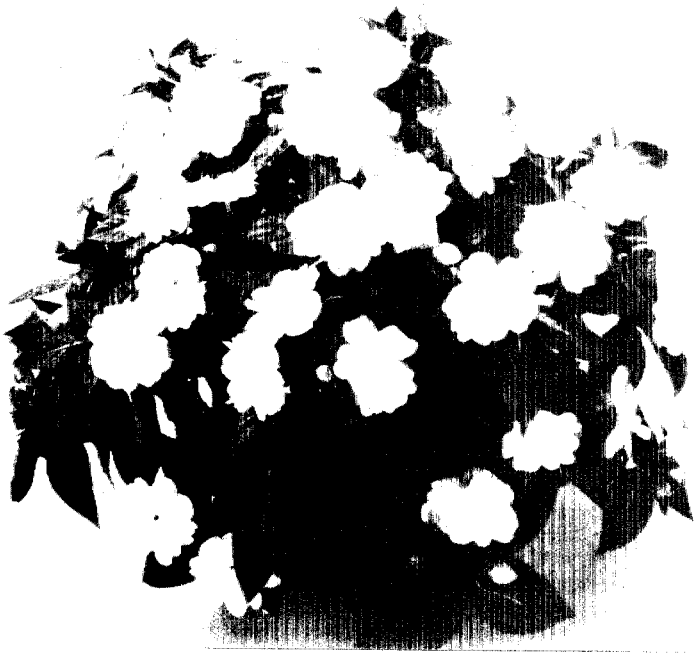

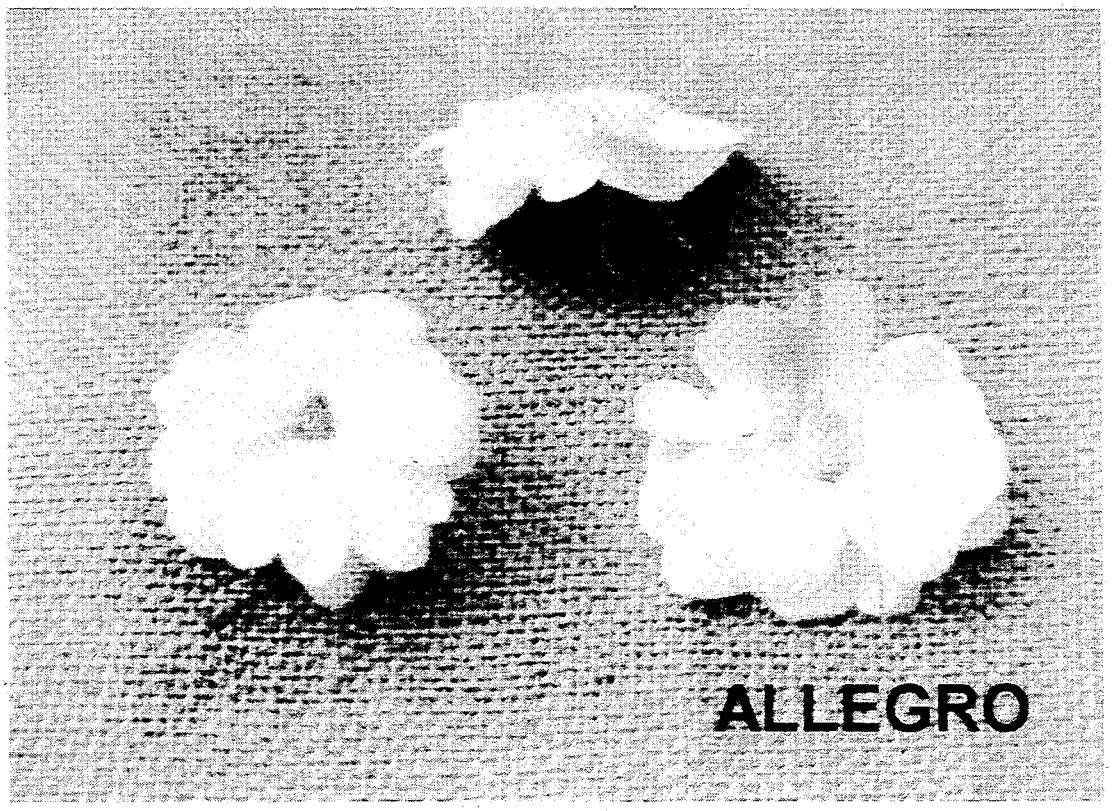
ALLEGRO